US012589180B2

(12) United States Patent　　　(10) Patent No.:　US 12,589,180 B2

Ghuge　　　　　　　　　　　　　　(45) Date of Patent:　　Mar. 31, 2026

(54) MEDICAL DEVICE HAVING A POLYMERIC NANOCOMPOSITE ACTIVELY CONTROLLED FOR RAPID HEALING OF FRACTURES AND SOFT TISSUE INJURY

(71) Applicant: Sleep Solutions of Texas, LLC, Tyler, TX (US)

(72) Inventor: Raghavendra Vitthalrao Ghuge, Tyler, TX (US)

(73) Assignee: SLEEP SOLUTIONS OF TEXAS, LLC, Tyler, TX (US)

( * ) Notice: Subject to any disclaimer, the term of this patent is extended or adjusted under 35 U.S.C. 154(b) by 57 days.

(21) Appl. No.: 18/628,279

(22) Filed: Apr. 5, 2024

(65) Prior Publication Data

US 2024/0335583 A1　　Oct. 10, 2024

Related U.S. Application Data

(60) Provisional application No. 63/494,799, filed on Apr. 7, 2023.

(51) Int. Cl.
　　*A61L 15/14*　　　　(2006.01)
　　*A61L 15/10*　　　　(2006.01)
　　*A61L 15/12*　　　　(2006.01)
(52) U.S. Cl.
　　CPC .............. *A61L 15/14* (2013.01); *A61L 15/10* (2013.01); *A61L 15/12* (2013.01); *A61L 2400/12* (2013.01)
(58) Field of Classification Search
　　CPC .......... A61L 15/14; A61L 15/10; A61L 15/12; A61L 2400/12; A61N 1/326; A61N 1/0464; A61N 1/205; A61F 5/0118; A61F 5/013; A61F 5/05858; A61F 5/0585; A61F 5/0102; A61F 13/00; A61F 13/00008; A61F 13/00021; A61F 2013/00089; A61F 15/004; A61F 13/043; A61F 13/041

See application file for complete search history.

(56)　　　　　References Cited

PUBLICATIONS

Tuan et al. "Development of a System for Real-Time Monitoring of Pressure, Temperature, and Humidity in Casts," Sensors 2019, 19(10), 2417. May 27, 2019 (May 27, 2019). Retrieved on Jul. 2, 2024. Retrieved trom entire document (Year: 2019).*

Bex et al., Growth hormone and bone health, Pubmed, 2003, 60 Suppl 3:80-6. doi: 10.1159/000074507.

Trippel, Potential role of insulinlike growth factors infracture healing, Clinical Orthopaedics and Related Research, Oct. 1998, pp. S301-S313, vol. 355.

(Continued)

*Primary Examiner* — Ophelia A Hawthorne

(74) *Attorney, Agent, or Firm* — FisherBroyles, LLP; Susan M. Oiler

(57)　　　　　　ABSTRACT

Medical devices having a controller in operative communication with a polymeric nanocomposite treatment device are disclosed. The polymeric nanocomposite treatment device includes a layered construction having a top layer and a bottom layer, which both include a matrix variable density polytetrafluoroethylene, a layer of carbon nanostructures juxtaposed to one each of the top layer and the bottom layer, and an electronic network layer between the two layers of carbon nanostructures. The electronic network layer includes a quantum micro-chiplet (QMC) or an octagonal quantum micro-chiplet integrated with a photonic integrated circuit.

13 Claims, 11 Drawing Sheets

(56)             References Cited

PUBLICATIONS

Syed et al., Pulsed electromagnetic fields for the treatment of bone fractures, Bangladesh Med Res Counc Bull, Apr. 1999, pp. 6-10, vol. 25 issue 1.

Anthem BlueCross, Clinical UM Guideline Ultrasound Bone Growth Stimulation, Jul. 6, 2022, 12 pages.

International Search Report and Written Opinion, Application No. PCT/US2024/023178, Jul. 15, 2024, 8 pages.

International Search Report and Written Opinion, Application No. PCT/US2024/023209 Jul. 10, 2024, 7 pages.

* cited by examiner

MEDICAL DEVICE HAVING A POLYMERIC NANOCOMPOSITE ACTIVELY CONTROLLED FOR RAPID HEALING OF FRACTURES AND SOFT TISSUE INJURY

RELATED APPLICATIONS

This application claims the benefit of U.S. Provisional Application No. 63/494,799, filed Apr. 7, 2023, which is incorporated herein by reference in its entirety.

TECHNICAL FIELD

This application relates to medical devices, in particular, medical devices having a polymeric nanocomposite device positionable at a treatment site and in operable communication with a controller, wherein the polymeric nanocomposite device has interleaved carbon nanotube or carbon nanodot matrix layers and at least one exterior layer comprising a matrix variable density polytetrafluoroethylene.

BACKGROUND

Typical fracture healing time is 3-4 weeks for the wrist and 4-6 weeks for tibia and fibula fractures. Fractures that require external fixation may take longer due to steel or other hardware. Compound exposed (open) fractures take 3-4 weeks longer to heal than closed fractures, typically due to a break in skin and tissue infections. And, surgical interventions to stabilize fractures are often necessary, which will again increase the complexity of care and the number of weeks for healing.

While a fractured bone is healing, the person may suffer from hardships and/or complications, such as disrupted sleep, weight gain, immobility, deep vein thrombosis, pulmonary thrombo-embolism, risks of nerve paralysis, sepsis, disseminated intravascular coagulation, and avascular necrosis.

There is a need to heal fractures more quickly, which will reduce the risk of complications inherently or synergistically. The goal is faster patient rehabilitation and return to normal activity.

SUMMARY

In a first aspect, medical devices are disclosed that have a controller in operative communication with a polymeric nanocomposite treatment device. The polymeric nanocomposite treatment device has a layered construction: a top layer and a bottom layer both comprising a matrix variable density polytetrafluoroethylene, a layer of carbon nanostructures juxtaposed to one each of the top layer and the bottom layer, and an electronic network layer between the two layers of carbon nanostructures. The electronic network layer has a quantum micro-chiplet QMC or an octagonal quantum micro-chiplet integrated with a photonic integrated circuit. The electronic network layer has a power source in electrical communication with the quantum micro-chiplet and the photonic integrated circuit, and one or more of a sensor module, an electromagnetic field module, robotics module, an intravascular ultrasound module, and a vacuum module.

The sensor modules include one or more of a capacitive micromachined ultrasonic transducer (CMUT), a complementary metal-oxide-semiconductor (CMOS) based sensor, an infrared sensor, a fiberoptic sensor, a radioisotope sensor, a temperature sensor, and a pressure sensor.

The layered structure of the polymeric nanocomposite treatment device optionally has one or more of a sensor module, an electromagnetic field module, robotics module, an intravascular ultrasound module, and a vacuum module as a discrete layer interleaved by juxtaposed layers of carbon nanostructures positioned above or below the electronic network layer. Each such discrete layer, when present, is in operative communication with the electronic network layer.

In all embodiments, the medical device can include a treatment site covering configured to hold the polymeric nanocomposite treatment device against a treatment site of a user. In some embodiments, the treatment site covering is selected from the group consisting of a wrap, a band, a brace, a cast, and a bandage.

In all embodiments, the medical device can include a tether operatively connecting the controller to the polymeric nanocomposite treatment site device. The controller is mateable to a first end of the tether and is lockable thereto by a primary lock comprising an expandable male member of either the controller or the tether and a secondary lock configured to opened before the primary lock can be opened. The expandable male member has a compression spring in compression between radially opposing drivers, and the radially opposing drivers are in operative mechanical communication with a security nut. Rotation of the security nut activates opposing rods to push the radially opposing drivers toward one another, thereby compressing the compression spring and reducing the size of the expandable male member to render it removable from either the controller or the tether.

The tether can have carbon nanostructures configured for electrical and/or thermal communication between the controller and the polymeric nanocomposite treatment device. The tether can have electrical connections and conduits configured for operative communication between the controller and the polymeric nanocomposite treatment device.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present system.

DETAILED DESCRIPTION

Figure 1:
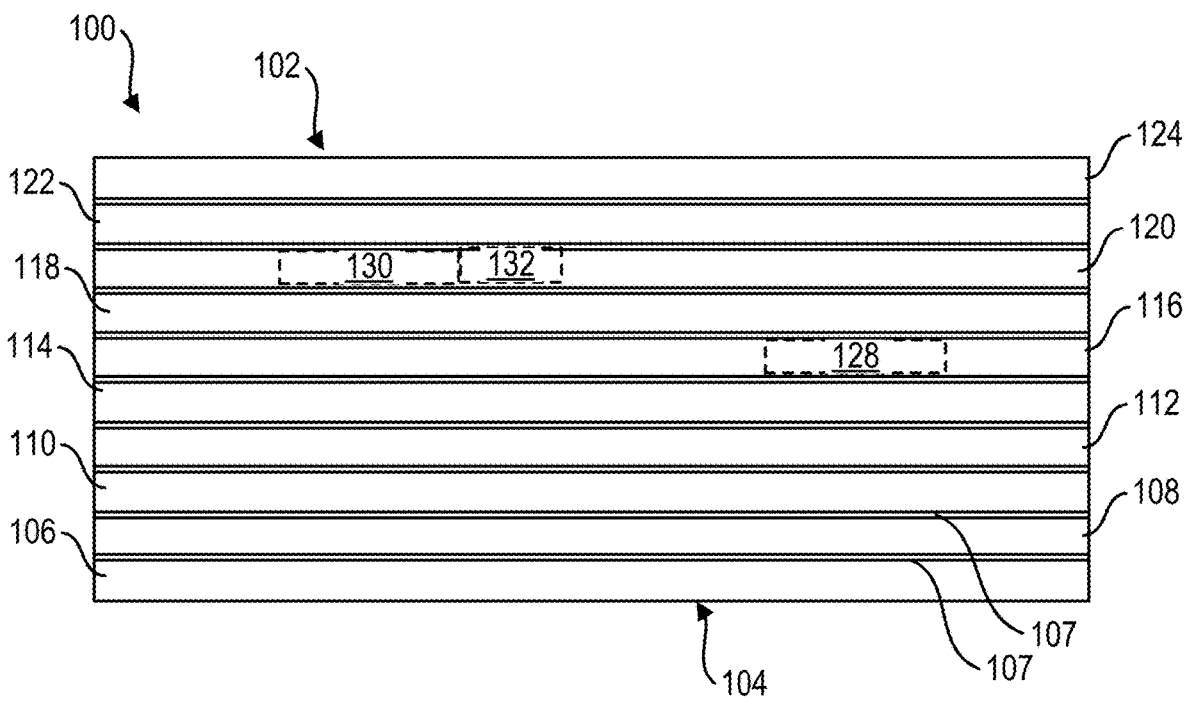
FIG. 1 is a cross-sectional representation of a first embodiment of a polymeric nanocomposite device.

The following detailed description will illustrate the general principles of the invention, examples of which are additionally illustrated in the accompanying drawings. In the drawings, like reference numbers indicate identical or functionally similar elements.

While the examples discussed herein are for tibia-fibula fractures, this is meant to be non-limiting. The device can be shaped to rest against any bone in need of a fracture repair, including, but not limited to, closed fractures, compound fractures, non-displaced fractures, displaced fractures, fractures with hardware used to stabilize bones, soft tissue injury, tendon injury, cartilage injury, and orthopedic sugary. The device may also be used to treat compartment syndrome, deep vein thrombosis, peripheral arterial disease, an arterial embolism, peripheral arterial surgery, peripheral venous surgery, limb salvage, vascular emergencies, crush injury management protocol, burn healing, decubitus ulcers, and post-limb reattachment surgery.

As used herein, "fluid" means any liquid, suspension, colloid, gas, plasma, or combinations thereof.

Figure 2:
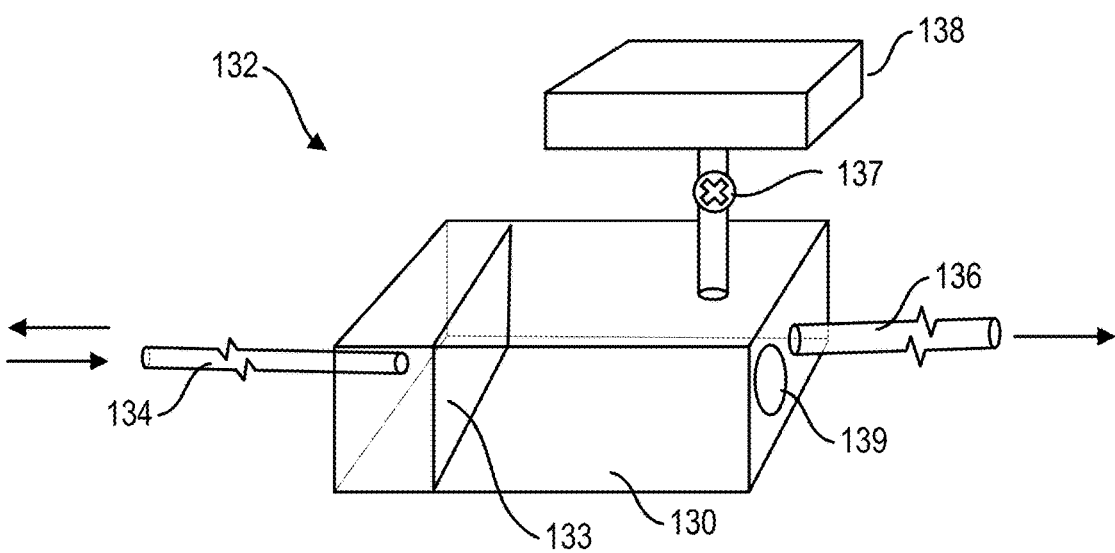
FIG. 2 is a dispenser for an active agent that can be present in the polymeric nanocomposite device of FIG. 1.
Figure 3:
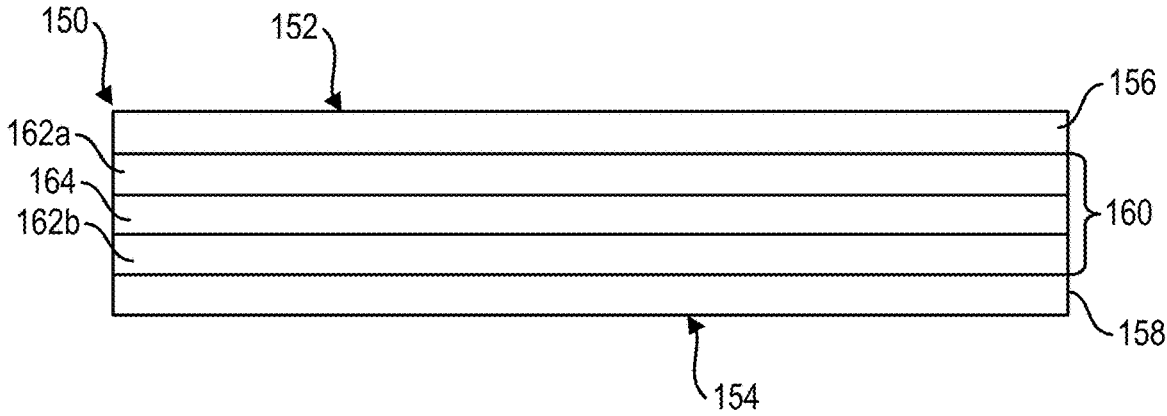
FIG. 3 is a cross-sectional representation of a second embodiment of a polymeric nanocomposite device.

Referring now to FIG. 1, a cross-sectional view showing the possible layers for a polymeric nanocomposite device 100 that may be in the form of a wrap, band, brace, or the like for positioning about a bone in need of fracture repair as exemplified in FIGS. 2 and 3 or against tissue or the like in need of repair. The interior layers 108 through 124 are not limited to the specific order represented in FIG. 1. Instead, the sequence of layers can be different and/or some layers may be optional, which is application dependent. Variation in the sequence of the layers 108 to 124 provide freedom for planning locations of conduits, channels, electrical connections, sensors, etc. The polymeric nanocomposite (PNC) device 100 has a treatment site contact surface 102 and an outermost surface 104.

While not shown in FIG. 1, each of the interior layers 108 through 124 are interleaved by a structural matrix 107 comprising one or more of carbon dots (CDs), carbon nanotubes (CNTs), shape memory alloys (SMAs), and shape memory polymers (SMPs). Interleaving such layers 107 in the device provide equal tensile strength in all direction allowing the shape memory alloys or polymers to be used, if present to adjust stiffness or elastic properties of the final product. Moreover, the innermost layer 124 and the outermost layer 106 can be customized based on the glass transition temperature of the material therein or based on the thickness of the layers to provide a desired elasticity or tensile property for the device. The ratio of SMAs or SMPs with a variety of glass transition temperatures or shape transition temperatures (Ttrans) allows us to create varying degrees of stiffness. The carbon nanotubes or carbon dots can define integrated circuits configured to provide processing of data in real time and transmission of data to a circuit or computer in operative communication therewith, such as a mobile phone, the internet, a tablet, a computer, or mobile or dedicated app technology stored in any appropriate means of technology.

The treatment site contact surface 102 is defined by an innermost layer 124. In one embodiment, the innermost layer 124 is a selective conductive layer that is operatively connected to various of the inner layers to provide active treatment to a target site, such as a bone in need of healing. This innermost layer 124 may deliver heat (i.e., provide warming or cooling), air, ultrasound, pressure, an electromagnetic field (steady state or pulsed), radiation, chemical, drug, or a combination thereof to the target site. This layer can actively open inter-cellular pores of the skin and/or generate carrier-facilitated transfer of chemicals, biological materials, nanomaterials. In one embodiment, the innermost layer 124 has elastic properties that enable it to conform to a surface of the target site. This layer 124 may also include infrared photography, oxygen concentration monitoring, blood flow monitoring. etc. The sensors that measure blood flow, oxygen concentration or delivered infrared signals and capture, measure sodium, potassium, chloride, bacterial count are in this layer and they in turn are connected through the network of nanotubes to ultimately the controller discussed in detail herein.

The outermost surface 104 is defined by an outermost layer 106. The outermost layer 106 is made up of double layered elastic material such as medical compression stockings, neoprene, SPANDEX® material, latex or rubber or combination of these materials, or knitted materials like cotton, polyester or wool, or TEFLON™ fluoropolymers, forming a flexible supportive layer configured to provide the ability for the polymeric nanocomposite device 100 to conform to a surface of the body of a user or wrap about a portion of the body of the user, such as an arm or leg or chest.

The outermost layer 106 and the innermost layer 124 may comprise a material that is reusable, in particular a material that can be sanitized and reused. These layers can be made of or comprise polytetrafluoroethylene (PTFE), also known as TEFLON™ fluoropolymers. The PTFE may be a matrix variable density PTFE. The matric variable density PTFE will contain variable customizable ratios of e-PTFE, d-PTFE, n-PTFE. c-PTFE has larger pores, d-PTFE is dense and has sub-micron pores, and n-PTFE is highly dense. d-PTFE is used in bone and tissue regeneration, and n-PTFE is used in grafts. The matrix variable density PTFE can have e-PTFE to d-PTFE in a ratio in a range of 4:1 to 1:4. Both of these layers 106, 124 have a thickness in a range of 10 μm to 1000 μm, more preferably 20 μm to 100 μm.

Still referring to FIG. 1, interior layer 108 is an interstitial layer configured to carry hardware, such as tubes, wires, vacuum channels, pressure channels, ducts supported with a significant amount of polymer for physical protection and protection of unique product being delivered. This layer can be made of or includes a matrix variable density PTFE layer. A quantum micro-chiplet or an octagonal quantum micro-chiplet is integrated with a photonic integrated circuits (OMC/PIC or QMC/PIC) for layer 110, which is an optional layer. In another embodiment, such hardware can be housed in the controller 202 (discussed in more detail herein) while signals and commands will be transmitted to and from the layers, including interior layer 108. Such chips and circuits have been developed by MIT. A QMC emits single-photon pulses that are routed and manipulated by photonic integrated circuits. Layer 110 can be in the form a diffuse or focal matrix of such chips and circuits configured to regulate and control precise delivery and recovery of data and products. Layer 110 is in electrical communication with a second QMC/PIC in a controller 202 of a therapeutic device 200 shown in FIG. 3. The QMC can be available from Zhongke Quantum Technology (Hunan) Co., Ltd.

Layer 112 can be a thermal sensory layer, which has the primary function of regulating temperature at the treatment site, such as a bone, muscle, tendon, cartilage, skin, etc. Regulating temperature includes measuring the temperature at the treatment site, and heating or cooling the treatment site to maintain the treatment site at a preselected temperature at which healing is maximized. The temperature is measured using a sensor suitable for monitoring temperature and the data collected by the sensor is in electrical communication with a transmitter, an integrated circuit, or other electronics that receives the data and can activate the heating or cooling function.

Layer 114 comprises at least one frequency sensor and/or deliver systems. The frequency sensor can be one that senses optical frequencies and/or photonic frequencies. Example sensors include a capacitive micromachined ultrasonic transducer (CMUT), a complementary metal-oxide-semiconductor (CMOS) based sensor, infrared sensor, fiberoptic sensor, radioisotope sensor, and other radiation sensors. The CMUT may be in the form of a micromillimeter circular disc(s), terminals at predetermined locations, or a tubular distribution as described below with reference to FIG. 6 or 9, and combinations thereof. This layer will be insulated from the exterior layers, to avoid the external environment from interfering with the sensors. Layer 116 is a pressure application layer. Layer 116 includes a means to apply pressure to the treatment site and can include a pressure sensor (unless the pressure sensor is in one of the other layers, such as layers 112 or 114). Regulating pressure includes measuring the pressure applied by the treatment device 200 at the treatment site, and adjusting the pressure applied to the treatment site to maintain the treatment site at a preselected pressure at which healing is maximized and deep vein thrombosis is avoided. The pressure is measured using a sensor suitable for monitoring pressure and the data collected by the sensor is in electrical communication with a transmitter, an integrated circuit, or other electronics that receives the data and can activate the means to apply pressure. The pressure sensor can be any commercially available pressure sensor or hereinafter developed pressure sensors. In one embodiment, a hydrophobic carbon dot nanoparticle (f-CD) mixed with polyvinyl alcohol and catechol-conjugated chitosan in the form of a hydrogel is suitable for a pressure and vibration sensor as taught by Professor Ryplida of the Department of Green Bio Engineering of Korea National University of Transportation in the Republic of Korea. Information about how much pressure is being applied by various tissues will be recorded and used in AI algorithms. Sensors will measure impact of tensile force created inside the cast. The pressure application system can be accomplished via this layer 116 comprising a ratio of SMAs or SMPs that have a variety of glass transition temperatures or shape transition temperatures (Ttrans) so that varying degrees of stiffness (thereby creating different degrees of pressure) are possible by activation on one or more thereof.

The pressure system(s) in layer 116 can be coupled with a mechanical wire system. Pressurized channels or tunnels will be incorporated in this layer and any layers between the same and the treatment site contact surface 102. This channel/tunnel system will have sensory valves at location of each adapter or interconnect to confirm adequate functionality and safety.

In another embodiment, the pressure application layer 116 and/or the protective innermost layer 124 has elastic properties and/or differential thickness of the polymer defining the respective layer. The differential thickness is determined relative to the structure and density of a bone or other feature of a treatment site in need of healing to map greater thicknesses relative to an area in need of more pressure than a second area proximate thereto. The areas of increased thickness can be polymer alone or can include a metal component. This type of pressure is referred to herein as mechanical pressure.

In another embodiment, layers 116 or 124 can include a bladder 128, still referring to FIG. 1, in fluid communication with a source of fluid, such as a gas, liquid, etc. In one embodiment, the fluid is air, water, or a saline solution. The source of fluid can be present in the controller 202 of FIG. 7 or can be operatively connected thereto, and the tether 206 can include a conduit providing the fluid communication therebetween. The tether 206 can include additional means of communication 208 between the controller 202 and the polymeric nanocomposite device 250.

The pressure applied to the treatment site can be constant or pulsed. The pressure can be applied intermittently, for short periods of time, such as 5 minutes up to four hours, or for long periods of time such as four hours up to twelve hours or more as prescribed by a medical professional. One example of intermittent use is the application of pressure only during sleep, for four to eight hours, and it can be constant or pulsed during this intermittent period of time. Both examples of pressure application are suitable for providing progressively increasing pressure to stimulate directional bone growth. Sequential or simultaneous incremental pressure application is done over a period of hours to days to create stress on bone and thus direct growth and bone density in a certain area or direction of bone. This may depend on the location of fracture and the amount of stress the bone will be subjected to once functionality is restored. The bladder 128 provides for a more controlled means of applying pressure.

Layer 118 is configured to produce an electromagnetic field (EMF), which may be a pulsed EMF if desired. The EMF is provided to the treatment site for the promotion of healing to the bone, soft tissue, and/or skin. The EMF can be applied similar to the application of pressure; it can be constant or pulsed, and optionally for intermittent time periods. In one embodiment, EMF is delivered using the assembly described in detail with respect to FIG. 6. The EMF pulse is generated in the controller and is delivered locally through individual tubes. This pulse can have varying strengths applied through various tubes and various locations in the tissue or skin or bone. In another embodiment carbon nanotubes in the interleaved layers can be used to generate the EMF. The carbon nanotubes can be positioned in localized areas. In another embodiment, the EMF can be remotely applied using a generator 222 in the controller 202 of FIG. 3 and sent to, via the tether 206, to local electrodes at specific locations within layer 118, positioned strategically relative to the treatment site. EMF locally enhances circulation, oxygen delivery and promotes healing. Layer 120 is configured to dispense an active agent, such as a medication, vitamin, imaging agent, etc. and to provide electrical connectivity to the treatment site. To dispense medication, in one embodiment, layer 120 can comprise collagen carbon dot nanocomposites as described in co-pending Patent Application No. 63/494,794, filed Apr. 7, 2023 or conduits in fluid communication or delivery communication with a reservoir of an active agent. Layer 120 can include shape memory materials, such as alloys or polymers, activable by pH, temperature, magnetic field, or light. In this layer, the activation of a SMA and/or SMP is configured to open one or more pores in this layer and any layers in contact therewith and lying between layer 120 and the treatment site contact surface 102, such as layers 122 and 124 in FIG. 1.

Layer 120 can include a reservoir 130 that contains the active agent. A dispenser 132, for example as shown in FIG. 2, can be in operative communication with the reservoir 130. The dispenser can include a dispensation aqueduct system for aerosolized or liquid or gaseous therapeutic medications or testing materials or radioactive material or sealed compressed gas or liquid. In this self-contained device 200, data from sensors and feedback from mechanical system will be stored in on-board memory and/or transferred to a controller station and to proprietary software at a remote location, such as the controller discussed below with respect to FIG. 7 or the electronics disclosed in Applicants granted U.S. Pat. No. 11,484,435, which is incorporated herein by reference in its entirety.

Turning now to FIG. 2, the dispenser 132 has a hydraulic piston 133, operable in response to inflow and outflow of fluid through conduit 134. The hydraulic piston 133 is in operative contact with the reservoir 130 to push an active agent from the reservoir through outlet conduit 136. The hydraulic fluid can be a saline solution but is not limited thereto. The outlet conduit 136 can be in direct fluid communication with the treatment site or in fluid communication with a distribution system within a medical device. If reservoir 130 holds a single dose, after dispensing of the single dose is complete, the hydraulics or other means pull the piston back to a pre-dispensing state. Once in the pre-dispensing state, as shown in FIG. 2, a one-way valve 137 can be opened to release a secondary dose of active agent from a secondary reservoir 138 into the initial reservoir 130. While a single secondary reservoir 138 is shown in FIG. 2, multiple reservoirs may be in operative communication with the dispenser 132 to dispense multiple active ingredients simultaneously or sequentially or together. In another embodiment, rather than the hydraulic piston 133, an electrical system or robotic piston (such as a piezo electrical motor activated by electronic impulse) can be present to dispense the active agent.

All processes related to the dispensing system as well as other processes related to this invention use blockchain technology and NFT's (non-fungible tokens) in the computing process of the controller so as to create an immutable ledger of all events. Such data recording shall also direct or activate processes through artificial intelligence and/or robotics to perform all tasks and follow all algorithms and commands in an error-free environment. The record-keeping of the blockchain and NFTs will be available to the controller, the medical device, the cloud, a patient's medical electronic health record, mobile electronic devices (such as cell phone, tablets, laptops, watches, etc.), mobile APP's, etc. This data utilizes Web3 and Decentralized Finance (DeFi) or conventional billing methods to log each process and its associated billing in the hospital system or healthcare facility so as to provide error-free charging of financial aspect of the technology and its use to third party insurers and payors.

The dispenser 132 may include a means for activating an activate agent 139, such as a source of radiation, such as UV light, a source of heat, a LASER, or whatever else is required to activate certain active agents. In another embodiment, the dispenser 132 includes a feedback loop sending a signal to an on-board or external controller upon dispensing an active agent to activate a secondary means of activation, whether included in the medical device or external to the medical device.

The connectivity of layer 120 is provided by electrical leads or carbon nanostructures that are positioned to connect with the treatment site and are in electrical communication with QMC/PIC of layer 110. Such connectivity is provided by conventional electrical, electronic, low voltage methods in one embodiment. In another embodiment it may utilize nanotubes (CDT's/CNT's) to conduct or transfer data through non-conventional methods utilizing their selective or preferential signal transmission properties. It may use a combination of both, conventional and nanotechnology. The circuits for these structures may be conventionally manufactured or may utilize 3D printing with new resins that contain nanotubes (CNT's/CDT's) described below or utilize new Robotic Hybrid 3D multi-material printer described in this invention or utilize prior art methods from industrial circuit board printing that utilize 3D printing such as described by Dassault Systems SolidWorks corporation. The various layers of this device (invention) may entirely be printable using 3D printing or may be assembled on an assembly line using a combination of manufacturing methods for individual layers. Layer 120 can also be configured to conduct fluid analysis and for detection of bacterial colony count.

Layer 122 is configured to provide vacuum, suction, and microbe measurements. Layer 122 includes conduits open to the treatment site contact surface 102 and in fluid communication with the exterior environment, thereby functioning as a natural drain, or in fluid communication with a pump 230 position in the controller 202 (see FIG. 7). The aspirator system can include an injector for introduction of a saline solution to flush a treatment site and an aspirator to withdraw the contents flushed by the saline solution. In one embodiment, a dispensing system similar that disclosed in FIG. 2 can be present to introduce the saline solution and then suction up the flushed contents. The pumps, aspirators, controller, and valves are connected to measurement sensors that provide continuous feedback to the controller which regulates the precise volume, pressure and other properties of the dispensed materials and is in operative communication with active site of delivery so as to acquire information about the desired outcome and execution of each and every action. This sequence of events and information related to such events are all stored using blockchain technology and (NFTs. This data utilizes Web3 and Decentralized Finance (DeFi) or conventional methods to log each process and its associated billing in the hospital system or healthcare facility so as to provide error-free charging of financial aspect of the technology and its use to third party insurers and payors.

This layer will remove debris, liquid accumulation, fluids from the treatment site, if needed, such as open comminuted fractures and compartment syndrome. The vacuum aspiration system can be coupled with a mechanical wire system. Pressurized channels or tunnels will be incorporated in this lay and any layer between the same and the treatment site contact surface 102. This channel/tunnel system will have sensory valves at location of each adapter or interconnect to confirm adequate functionality and safety.

Layer 124 is a selective conductive, protective layer. Layer 124 may have an clastic property for conformity to the treatment site that can change as the treatment site reduces swelling during healing. The selective conductive property of the layer can be used to deliver active agents to the treatment site, to heat or cool the treatment site, provide air flow to the treatment site, provide pressure to the treatment site, provide the electromagnetic field of layer 118, provide ultrasound, infrared photography, oxygen concentration monitoring, and/or blood flow monitoring. This layer can include any or all of the structures, material, and features described above for the other layers. If more than one such is included in this layer, they can each be strategically positioned relative to the treatment site as selected by a medical professional.

The layers 106 to 124 can be manufactured using additive printing, which includes 3D printing. Here, one layer at a time can be printed and the next layer on top thereof, etc. 3D printing refers to the transformation of a digital CAD (Computer-Aided Design) file by a 3D printer into a three-dimensional physical solid object or part, i.e., the 3D printer "translates" the CAD file into a 3D model. The 3D printer typically does this by depositing material layer by layer in precise geometric shapes using a printhead, nozzle, or other printing technology. Each layer can be considered a thinly sliced cross-section of the final object being built. In another embodiment, the layers 106 to 124 can be manufactured by subtractive manufacturing methods. Subtractive manufacturing includes the controlled removal of material, for example, by milling, etching, machining, etc. In yet other embodiments, a hybrid approach may be taken as well (some materials by additive printing and others using other technologies).

Turning now to FIGS. 2-5, a second embodiment of a polymeric nanocomposite treatment device 150 is shown that has a layered construction having a top layer 155 defining a top surface 152 and a bottom layer 158 defining a bottom surface 154 both comprising a matrix variable density polytetrafluoroethylene. The layered construction includes a layer of carbon nanostructures 162*a*, 162*b* juxtaposed respectively one to the top layer 156 and the other to the bottom layer 158, and an electronic network layer 164 between the two layers of carbon nanostructures. The electronic network layer 164 sandwiched between the layers of carbon nanostructures 162, 16*b* is collective referred to as a network matrix 160. With reference to FIG. 3, the top layer 156 has a first thickness T1 that is typically in a range of 10 μm to 100 μm, the network matrix 160 has a second thickness that is typically in a range of 10 μm to 1000 μm, and the bottom layer 158 has a third thickness that is in the same range as T1.

Figure 4:
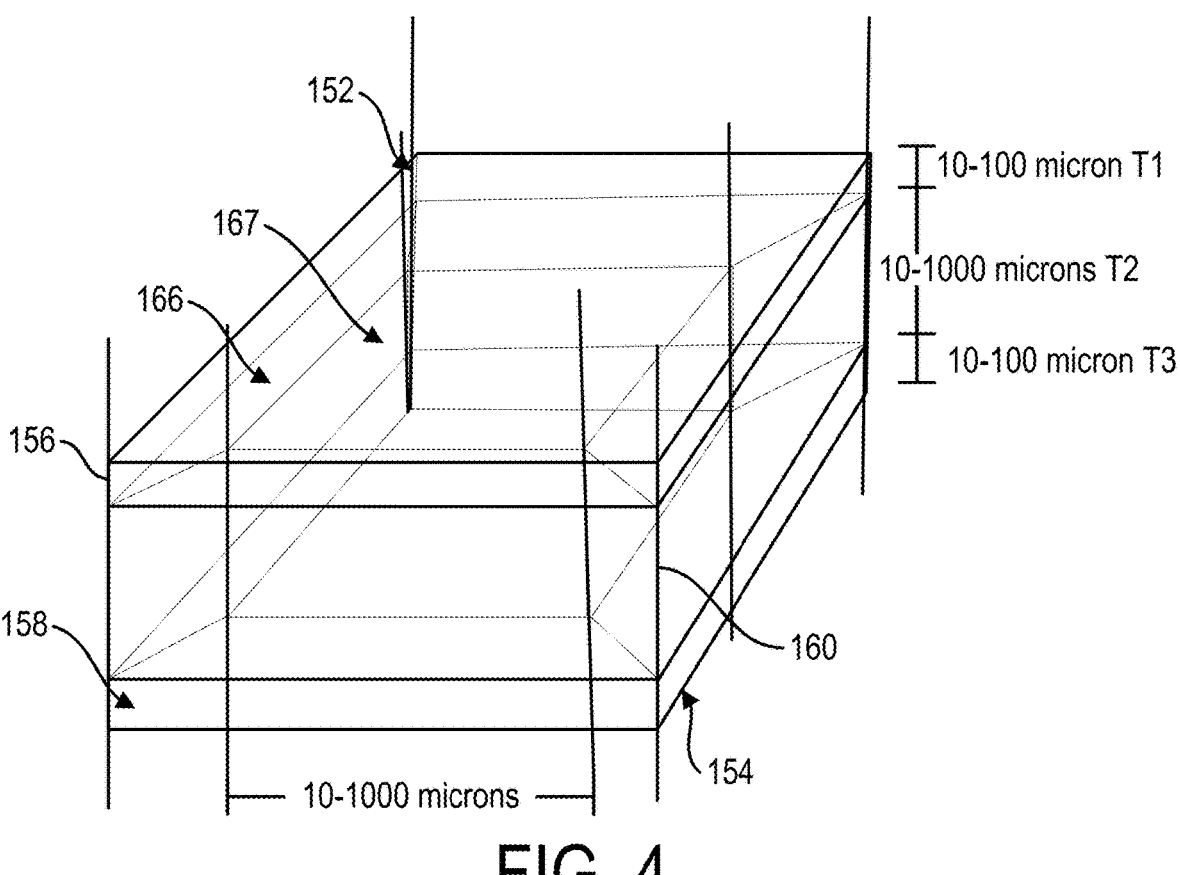
FIG. 4 is a side perspective view of the second embodiment of the polymeric nanocomposite device.
Figure 5:
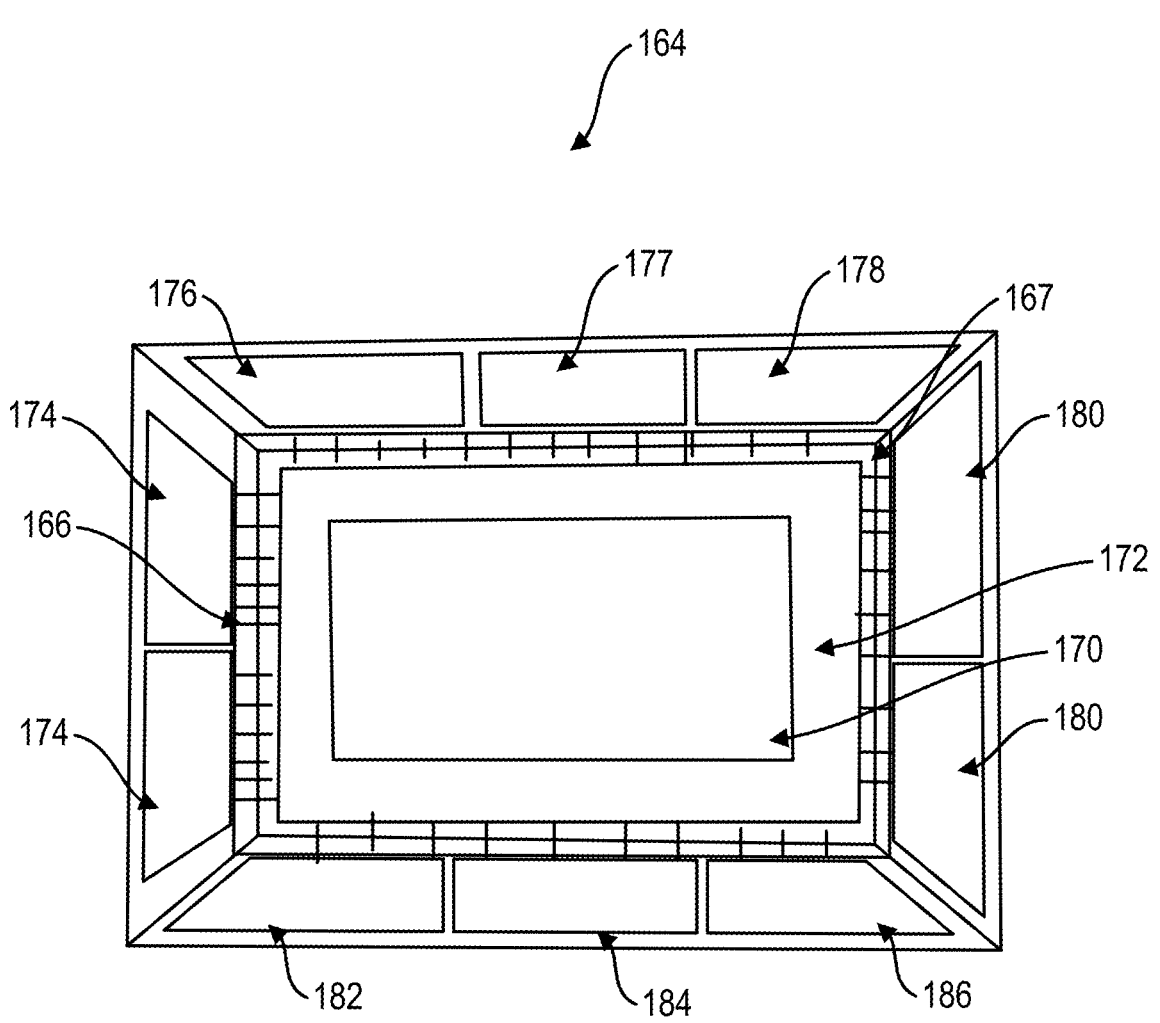
FIG. 5 is a top plan view of the network matrix layer of the second embodiment of the polymeric nanocomposite device.

In this embodiment, in contrast to the embodiment of FIG. 1 where discrete layers have discrete functions, any combination thereof can be included in the electronic network layer 164. With reference to FIGS. 4 and 5, the electronic network layer 164 is represented as having an integrated circuit base 166 with a core processor 167 that includes a quantum micro-chiplet 170 and a photonic integrated circuit 172. Arranged in electrical communication with the core processor 167 via the integrated circuit are one or more power sources 174, a plurality of modules, controllers, inputs/outputs, etc. For example, a first control module 176 is configured to receive inputs from sensors, such as temperature and pressure sensors and send outputs based thereon to operate mechanical components or systems of a medical device in which the same are incorporated, a second control module 177 is configured to receive inputs from sensors indicating operation of a mechanical component, such as the dispenser, and send outputs based thereon to operate said mechanical, a third control module 178 is configured to receive inputs from another sensor and send outputs based thereon to whatever mechanical component or system is in need thereof. A controller and/or emitter of CMUT and/or IVUS 180 can be present. A source of electromagnetic fields 182 (pulsed or non-pulsed) can be present. A module for infra-red, fiberoptic, radio isotope sensory inputs 184 and outputs to mechanical component or system is in need thereof can be present. A robotics controller 186 can be present for sending outputs to mechanical components or systems in need thereof. Each of these examples are in electrical and operative communication with the core process 167.

Figure 6:
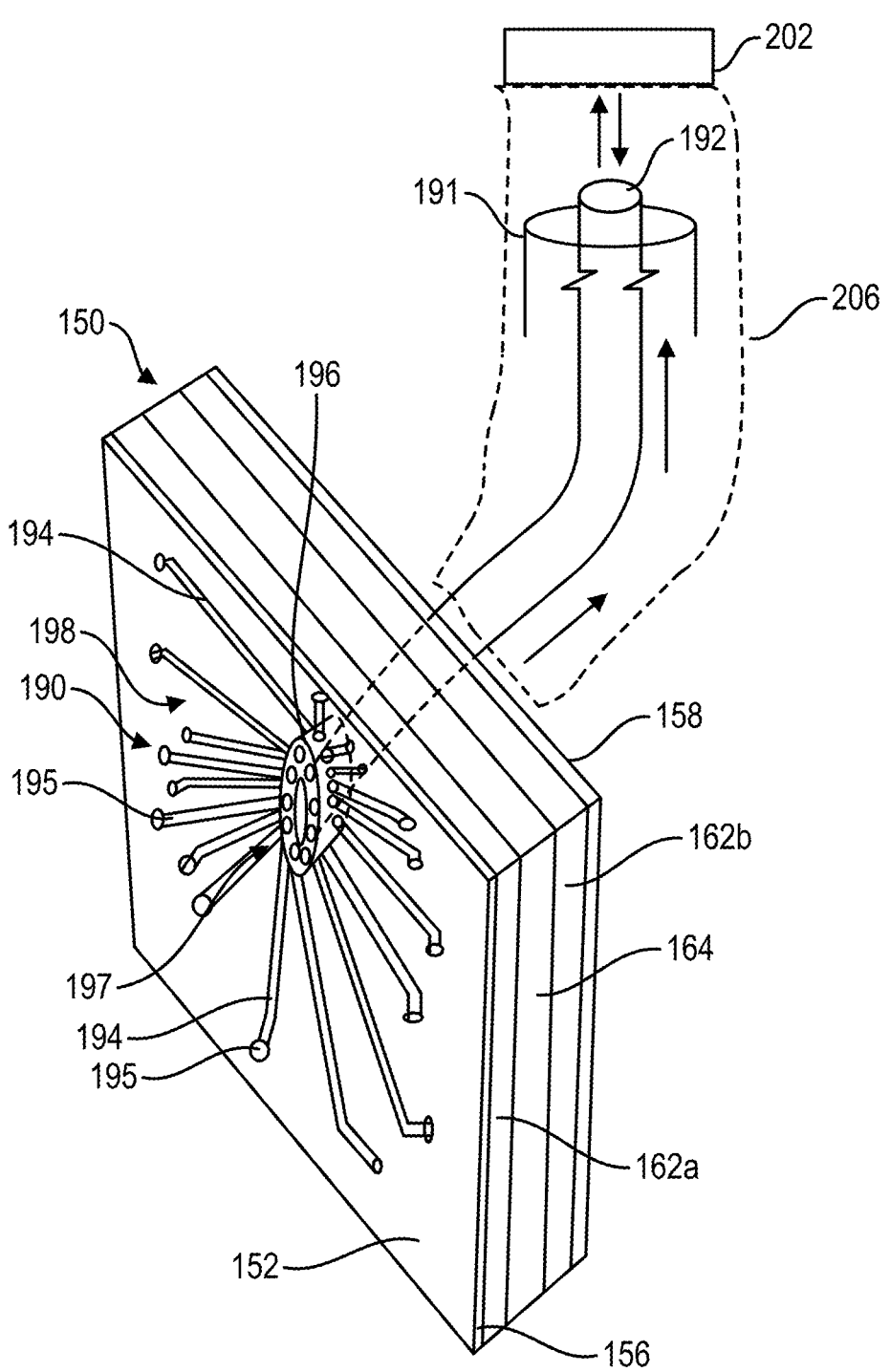
FIG. 6 is a longitudinal, cross-sectional, perspective view of an embodiment of a distribution system in a polymeric nanocomposite device.
Figure 7:
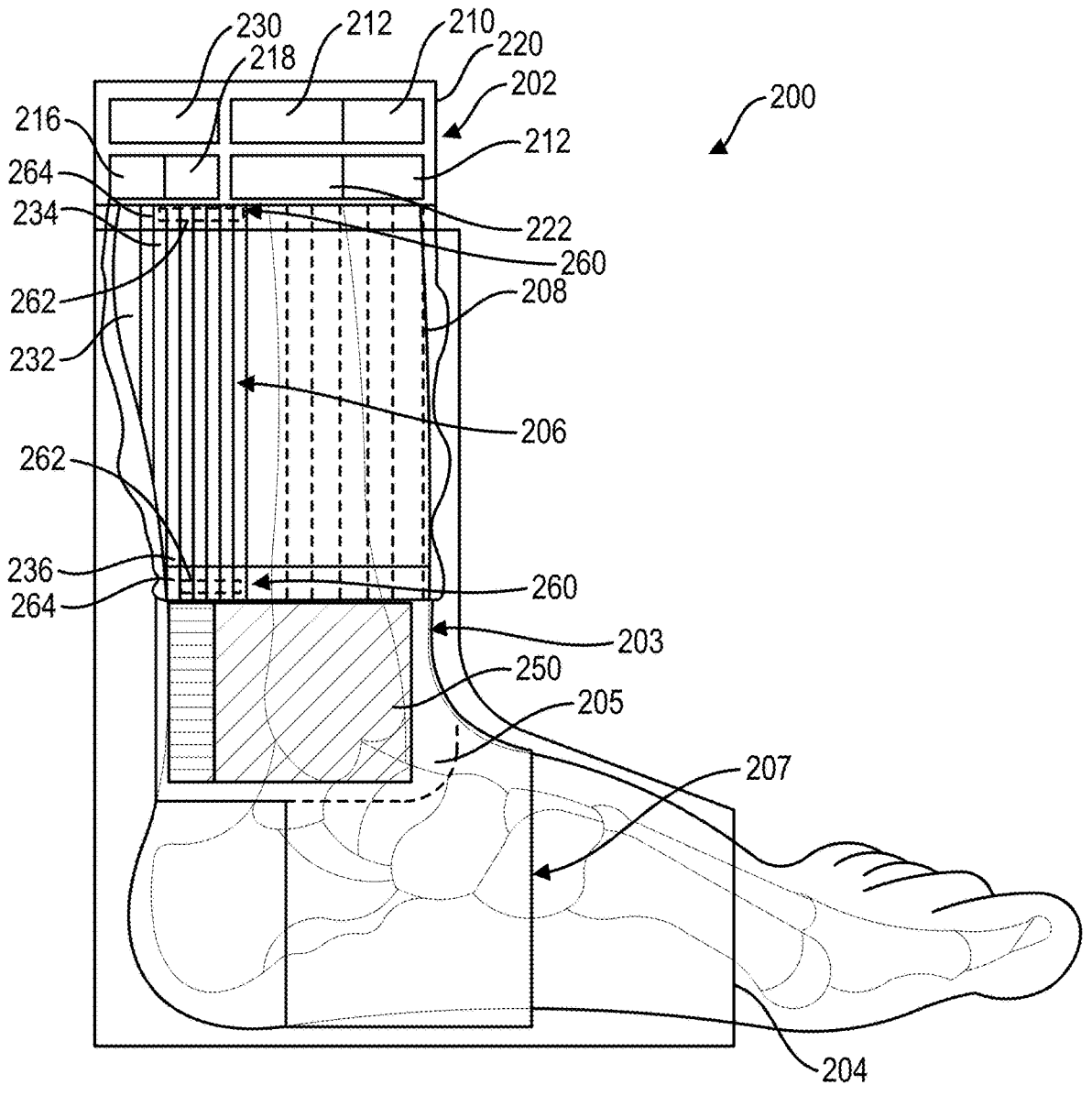
FIG. 7 is a first embodiment of a medical device that includes the polymeric nanocomposite device.

Turning now to FIG. 6, one embodiment of a configuration for delivery of any of the treatments disclosed herein to the treatment site and/or communication or transport back to a controller, such as controller 202 via a tether 206, described in detail herein with respect to FIG. 7, is shown. Such a system will be referred as distribution system 190. Individual channels 191 and tubes 192 are present in the tether to provide operative communication between the controller and the polymeric nanocomposite device 150. The channels 191 and tubes 192 are built out of conventional materials such as plastics (including, but not limited to polyvinyl chloride) or carbon nanotubes and may be formed in the material of any of the layers of the polymeric nanocomposite device.

As used herein, "channels" refer to conduits of larger size than "tubes." One or more "tubes" can be present inside a channel, i.e., pass through the channel. Each individual channel 191 has a diameter in a range of 1 mm to 10 mm. In some embodiments, the channels 191 are flexible but have a wall thickness of 1 mm to 2 mm. Each tube has a diameter in a range of 0.5 mm to 8 mm and a wall thickness in a range of about 0.5 mm to 1 mm. Any channels or tubes within the layers of the polymeric nanocomposite device can be formed by any know techniques, including etching (mechanical or chemical), machining, and molding.

Each channel 191 and each tube 192 can terminate in the top surface 152 with an open end, but more preferably terminate before reaching the innermost layer 156. In some embodiments, the channel 191 and the tube 192 terminate in the outermost layer 158. In other embodiments, the channel 191 and tub 192 can terminate either of the carbon nanostructure layers 162*a* or 162*b*. Depending upon the particular treatment to be accomplish by a particular channel and tube combination, the device can have one channel and tube combination that terminates in the outermost layer 158 and another that terminates in a different layer of the polymeric nanocomposite device 150.

Each tube 192 can have a carbon nanotube (CNT) lining. For some of the tubes the CNT lining can be configured for thermal treatment, other tubes have CNTs configured for EMF treatment, and yet other tubes have CNTs configured for water-proofing. Any number of channels 191 and tubes 192 can terminates into a head 196 that subdivides into a plurality of dispensing tubes 194 that each terminate in the top layer each with an open end 195. The head 196 can have numerous configurations depending upon the particular treatment to be delivered to the treatment site. In one embodiment, the head 196 has a shower head type configuration 197 and/or a starburst configuration 198. The dispensing tubes 194 carry fiberoptic light, LASER, UV rays, EMF, theragnostics, drugs, chemicals, or various sensors to the top surface 152. An active agent such as drugs, liquids, and theragnostics can be delivered to a respective open end 195 where it saturates the matrix variable density PTFE for interaction with skin, tissue or bone at the treatment site.

LASER, UV rays, thermal energy, and EMF can each be delivered to an open end 195 of a dispensing tube 194. If theragnostics are delivered through a separate and distinct patch or other means (outside of the polymeric nanocomposite device) to the local tissue or bone, once theragnostics are delivered to local site, they may be activated locally by delivering low light UV or LASER through the polymeric nanocomposite device.

Turning now to FIG. 7, a medical device, generally referred to by reference number 200, has a controller 202 in operative communication via a tether 206 with a treatment site covering 203, which has a polymeric nanocomposite device 250. The treatment site covering 203 can be a wrap, band, bandage, brace, or patch and optionally has a cast 204 surrounding the same when the treatment site is a bone in need of healing. The treatment site covering 203 can include a secondary portion 207 thereof that extends from a first portion 205 that seats the polymeric nanocomposite device 250 against the treatment site. This secondary portion 207 contacts an adjacent portion of the user's body to assist in holding the first portion 205 in its desired location. When the treatment site is an ankle, the secondary portion 207 can extend or wrap around the foot. When the treatment site is a wrist, the secondary portion 207 can extend or wrap around the hand. When the treatment site is a hand, the secondary portion 207 can extend or wrap around the wrist. The polymeric nanocomposite device 250 can include any of the layers discussed above with respect to FIGS. 1-5. The layers included can be tailored to meet the desired healing needs of the treatment site.

The controller 202 is operatively coupled to the polymeric nanocomposite device 203 but is typically not positioned inside the cast 204. Instead, the controller 202 is positioned outside the cast and can be removably attached to the user or the cast by any fastening means known or herein after developed. A few example fastening means include a strap with hook-and-loop material, hook-and-loop material, brackets with bolts or screws, wherein the cast has the brackets, and the like. The controller 202 houses a power source 210, a microprocessor or computer processing unit 212, which can include (i) non-transitory memory, (ii) a QMC/PIC, (iii) software that can include artificial intelligence programming, (iv) a cellular chip for transmitting data/signals and receiving data/signals, (v) an EMF processor, (vi) a CMUT processor, and (vii) a CMOS sensor processing unit, a medication dispensing system 214, an optical digital or fiberoptic receiver and transmitter 216, an infra-red imaging controller 218, and a pump 230 for vacuum and/or suction systems. The controller 202 will include external ports configured to repeatedly, replaceably connect to external dispenser systems, a source of radiation, such as UV radiation and/or a LASER, and IV infusion systems, just to name a few non-limiting examples. The controller can have a rigid housing 220 enclosing the above electronics or it can be incorporated into a flexible wrap that can surround the circumference of the extremity or part of the extremity of a user's body where the treatment site is located.

The power source 210 can be a standard or rechargeable battery or a port for accepting a plug connectable to a power source, such as an external battery or an electrical outlet. In one embodiment, the power source 210 is one or more rechargeable batteries in electrical connection with the other electronics of the controller 202 to power the same. The rechargeable batter may be a lithium-ion battery. In one embodiment, the lithium-ion battery is a nanoscale battery using a carbon-based material such as those available from Chasm a company headquartered in Canton Massachusetts. In another embodiment, the controller is configured to recharge the power source or power the power source based on transfer of body heat and/or static electricity of user's body through carbon nanotubes in the controller housing 220 or in the polymeric nanocomposite device 203. This is possible through Power Felt thermoelectric technology developed by Wake Forest University's Center for Nanotechnology and Molecular Materials. The carbon nanotubes are held in flexible plastic fibers that are made to feel like fabric.

Still referring to FIG. 7, the polymeric nanocomposite device 203 is positioned for direct contact of the treatment site contact surface 102, 152 of FIG. 1 or 3 with the selected treatment site. The polymeric nanocomposite device 250 is a multilayer device as described above with respect to FIG. 1 or 3 and can have any combination of said layers. The polymeric nanocomposite device 250 has one or more terminals for all modalities of monitoring, diagnostics, and therapeutics and will create two-way traffic to and from the controller 202, i.e., the device 250 is configured to send and receive electronic signals (data). The device 250 can any size, width, height, and dimensions required for an application to a selected treatment site. As discussed above, the device 250 and the covering 203 can have elastic properties for a secure fit to the treatment site and which allows adjustment for swelling (or the decrease thereof as healing occurs). The elastic properties can be attributed to the presence of the matrix variable density PTFE, elastic, rayon, rubber, nylon, and combinations thereof.

The mechanical system will be synchronized with CMUT/CMOS/EMF/PEMF or with or with any other technology that needs to go inside the cast or inside the tissue such as steel plates, screws. Mechanical system (wire, pressurized air, vacuum system, and other aspiration systems) can be placed for best effect at location of single site, or at multiple sites for skin applications, soft tissue applications such as aspiration system for removing accumulating fluids or to circulate cool air. Wire may have graded tensile strength to facilitate certain movements of certain targeted parts as opposed to other adjacent parts.

The tether 206 is a collection of all the connections from the controller 202 to the device 250. The connections include electrical connections, such as wires or electrodes, ports, conduits, ducts, tubes, fiber optics, etc. Any one or more of these can be insulated to reduce noise (sound), or prevent undesired transmission of EMFs, optics, waves, etc. to the environment. The connections can include a multi-layered matrix of carbon nanotubes, single walled or multi-walled or carbon nanodots. The tether 206 can be an independent elongate cord or it can be incorporated into an elastic sock 232. The elastic sock 230 is configured to protect the user's skin from a hard cast or brace and is configured to absorb sweat. In one embodiment, the sock 230 can circulate cool air to the area inside the cast or brace. In another embodiment, the sock 232 can be a compression sock configured to prevent deep vein thrombosis.

Still referring to FIG. 7, an interconnection mechanism 260 can be present between the controller 202 and/or a first end 234 of the tether 206 and between a second end 236 of the tether 206. In an alternate embodiment, one or both interconnections can be direct, nonremovable connections. In one embodiment, the connection between the second end 236 of the tether 206 and the polymeric nanocomposite device 250 is a direct, nonremovable connection and the connection between the controller 202 and the first end 234 of the tether 206 is a removable, interconnection mechanism 260. The interconnection mechanism 260 has mating male and female connectors 262, 264. The male connector 262 is shown as extending from the controller 202 in FIG. 7 and in FIG. 8, but it could be the reverse, i.e., extending from the tether 206. The interconnection mechanism 260 can be whatever size is needed to make all the electric/functional connections necessary for the polymeric nanocomposite device 250.

The interconnection mechanism can include a plurality of ports. There can be 2 to 20 ports, or even 2 to 20 ports, or more. Port can have a single specific function or can have dual or multi-functionality. Ports intended for fluid connections can be referred to as a "moat," especially when clustered together. Some ports may be used for infusing (sending a fluid to the treatment site). Some ports may be used for aspirating a fluid away from the treatment site, such as blood, fluids from the treatment site, excess infused fluids, etc. One or more ports may be attached to drains that are placed strategically for draining hematoma for example. In one embodiment, a redundant port for each functional port is provided as a backup. Ports may also be used as a conduit in which wires, fiberoptic, carbon nanostructures, or other types of connectors are fed to reach the polymeric nano-composite device 250. It is understood that such ports and a moat if present are hermetically sealed when the controller 202 and tether 206 are connected to one another.

Figure 8:
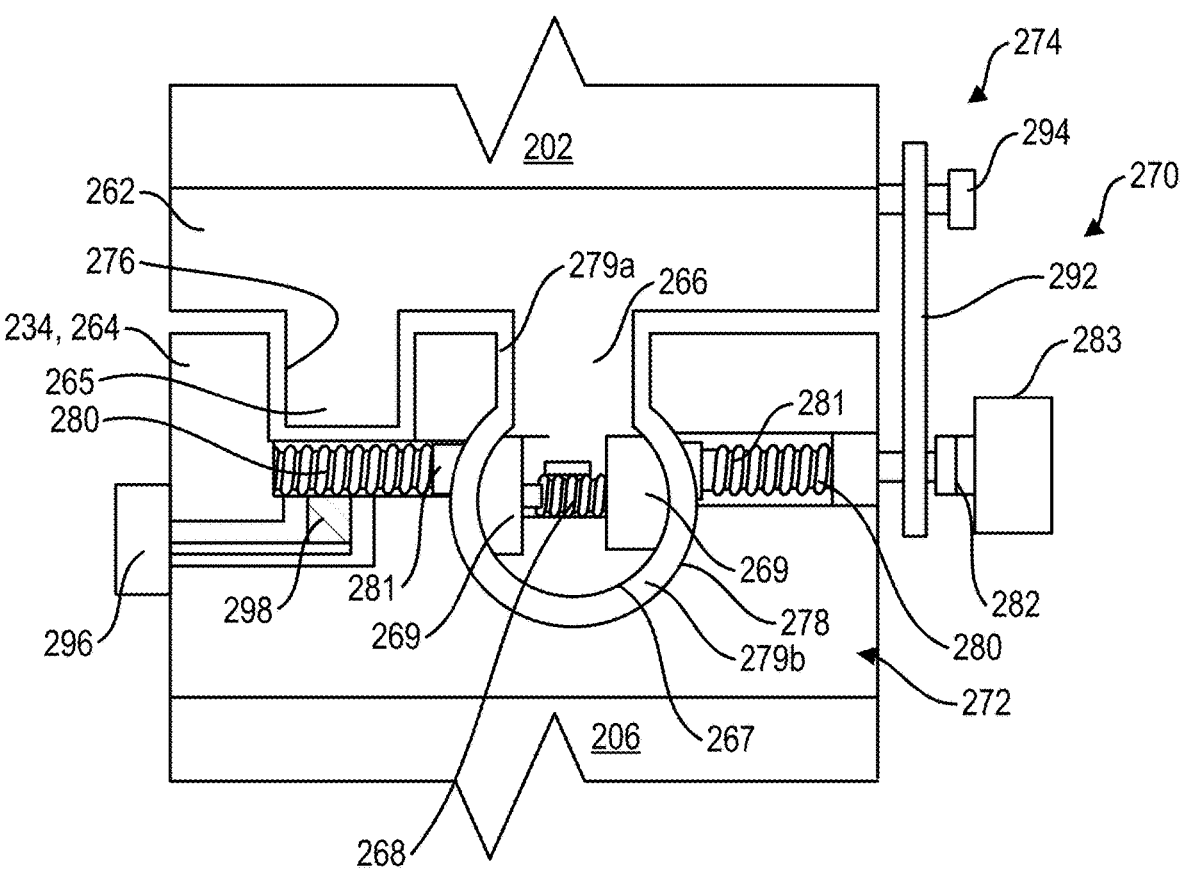
FIG. 8 is an enlarged view of one embodiment of an interconnection mechanism for the controller to the polymeric nanocomposite device.

Turning now to FIG. 8, an enlarged cross-section view of one embodiment of the interconnection mechanism 260 is provided. Here, the controller 202 has the male connector 262 that is insertable into the female connector 264 of the tether 206, which makes electrical connections between leads, carbon nanostructures, ducts, conduits, tubes, etc. The interconnection mechanism 260 includes a locking mechanism 270. The locking mechanism 270 has one or more primary locks 272 comprising double spring ball locks and a secondary lock 274 per primary lock to prevent accidental release of the primary lock. The male connector 262 has a registration protrusion 265 for mating to the female connector 264 and a protruding locking member 266 terminating with a radially expandable head 267. The expandable head 267 has a compression spring 268 sandwiched in compression between radially opposing drivers 269. The female connector 264 includes a registration socket 276, a locking socket 278 having an entrance 279a that is dimensionally smaller than an enlarged pocket 279b and opposing spring 280 and bolt 281 systems operable to linearly translate each bolt 281 into the enlarged pocket 279b when activated. In FIG. 8, the locking socket 278 and the expandable head 267 are spherically-shaped and mateable with one another. The expandable head 267, in its unexpanded state, is dimensionally small enough to pass through the entrance 279a and naturally expands to its expanded state, which is larger than the dimension(s) of the entrance 279a, once in the locking socket 278. The expandable head 267 and locking socket 278 is not limited to being spherically-shaped.

The registration socket 276 and the registration protrusion 265 can be elongate in shape, a single tab type shape, or a series of tabs. Regardless of the configuration, this connection can be hermetically sealed. These features are dimensioned to provide sufficient rigidity and stability to the connection between the controller and the tether. For example, lateral movement is prevented therebetween to protect the operative connections therebetween.

Still referring to FIG. 8, bolt 281 has a head 282 that is exposed at the exterior surface of the medical device 200. The head 282 includes a security nut 283 seated on or integral with the head. The security nut 283 has a keyway (not shown), thereby rendering the bolt rotatable only by introduction of a key into the keyway. The security nut 283 can be an elongate body that covers all bolt heads if a plurality of bolts are present. The security nut is configured such that turning the key clockwise squeezes the security nut onto each bolt head 282, thereby pressing inward on the security nut 283 depresses each and every bolt 281 simultaneously into the enlarged socket 279b to apply pressure on each of the drivers 269, thereby compressing spring 268 and rendering the expandable head 267 into an unexpanded state and removable through the entrance 279a of the locking socket 278. This unlocking of the head 282 of the primary locks 272 unlocks all the electrical interconnects, duct, and seals in preparation for separating the controller 202 form the tether 206 and/or the tether 206 form the polymeric nanocomposite device 250. The primary locks 272 are also electrically connected to an off switch in the controller 202 and optionally to an LED indicator such that the controller stops all treatments being administered to the treatment site by the polymeric nanocomposite device 250 and light the LED indicator, for example turning it red and indicating that the controller 202 can now be physically removed from the tether. Conversely, turning the key counter-clockwise expands the security nut and allows the spring-loaded bolts 281 to return to their starting position and allowing the expandable head 267 to expand if present. In this state, the LED is green, and the controller can be switched to being "on," automatically or manually.

Additionally, the bolt(s) 281 and security nut 283 is only rotatable after the secondary lock 274 is opened/removed, which prevents the expandable head 267 from accidentally being compressed during use. The secondary lock 274 has a spring-loaded latch having a latch 292 positioned behind each bolt head 282 between the bolt head 282 and the exterior of the medical device 200 and extending therefrom to a fastener 294 protruding from the controller 202. There can be one such secondary lock 274 or one per bolt head 282. The exterior surface can be defined by the medical device itself or a brace or cast positioned in surrounding fashion around the medical device 200. The fastener 294, can be a spring-loaded fastener, a screw/bolt, or a magnetic latch.

Still referring to FIG. 8, the registration socket 276 and the registration protrusion 265 can be magnetically latched to one another. This is accomplished by the presence of a magnet in one thereof and a ferromagnetic material in the other or mating magnetics in each thereof. The magnetic attraction therebetween is overcome by rotation of a turnkey 296 operatively connected to a lever 298 that moves to push the registration protrusion 265 from the registration socket 276. The turnkey 296 and lever 298 can be positioned wherever is most convenient for case of manufacturing and comfort of the wearer. Once the primary latch 270 is unlocked, the turnkey 296 can be turned to separate the controller 202 form the tether 206.

With respect to FIG. 8, any mechanical processes described can just as well be electronic processes. For example, one of the locks can be secured using a fingerprint scanner and electronic programming, passwords or through an App in an electronic device that is in communication with on-board electronics of a lock.

Figure 9:
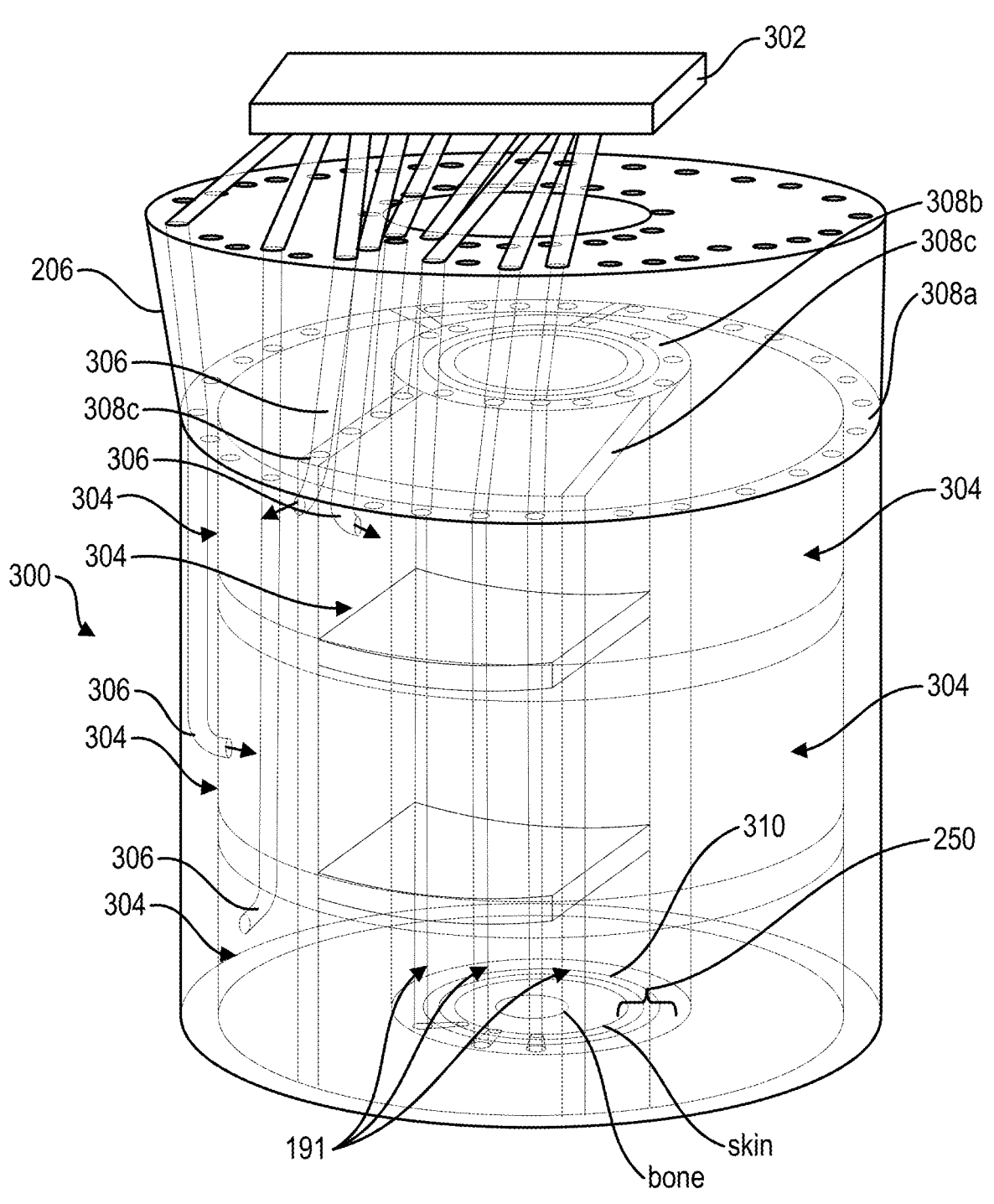
FIG. 9 is a side perspective view of a treatment device that includes a balloon system and a polymeric nanocomposite device.

Referring now to FIG. 9, the exterior surface of the tether 206 and/or the sock 232 can include a balloon system 300 for application of pressure to the treatment site. Here, a double layer structure is present, the inner being the polymeric nanocomposite device 250 from FIG. 7 and the outer being the balloon system 300 for application of compression against a treatment site. This balloon system 300 is in operative communication with an inflation controller 302, which may be part of controller 202 in FIG. 7 or can be independent therefrom. The balloon system 300 has a plurality of balloon chambers 304 that are distributed throughout the circumference of a treatment site covering. They are supplied by independent tubes 306 and inflated with a fluid. The fluid can be air, compressed air, saline, etc.

Individual channels 191 are built into the walls 308 defining the balloon chambers 304. The walls 308 can be an outermost wall 308a, an innermost wall 308b, and segment walls 308c. The individual channels 191 provide pathway connections to the tether as described in detail above, and tube, such as tubes 192 in FIG. 6, run through these channels to reach a dispensing system for treatment administration to the site in need thereof.

The balloon chambers 304 can be simultaneously increased or decreased in pressure by introduction or removal of the fluid. Sequential compression of the balloons provides the ability to sequentially compress the limb or tissue that the polymeric nanocomposite device 250 is wrapped around. This has multiple purposes. It can work like a compression stocking but mainly provides sequential stress to the underlying tissue and bone to accelerate healing. The polymeric nanocomposite device 250 can be attached to the inner surface 310 of the balloon system 300, for example using an adhesive and/or a stamping process. Stretch receptors can be incorporated into the walls 308 of the balloon system 300 for monitoring and feedback to the inflation controller 302.

Figure 10:
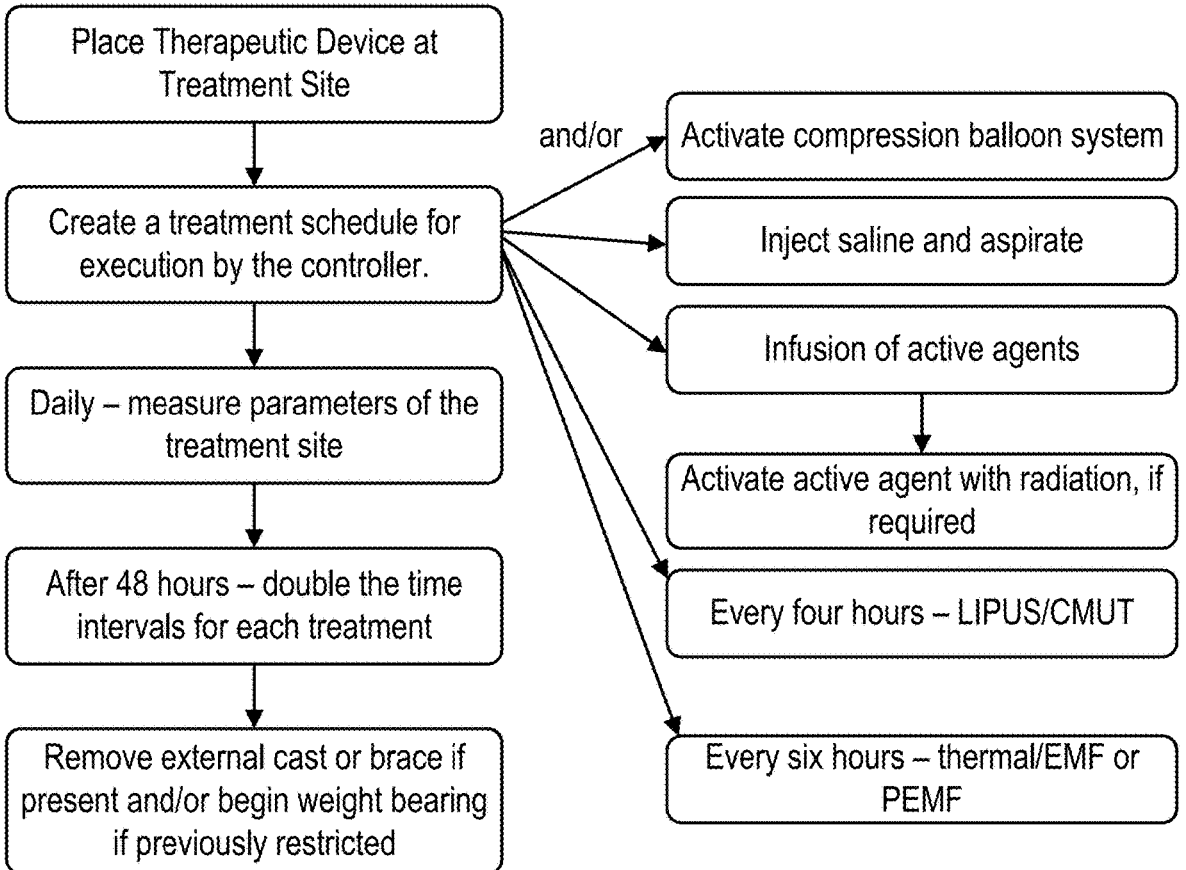
FIG. 10 is a flow chart proposing various methods of treatment for a treatment site using the medical devices disclosed herein.
Figure 11:
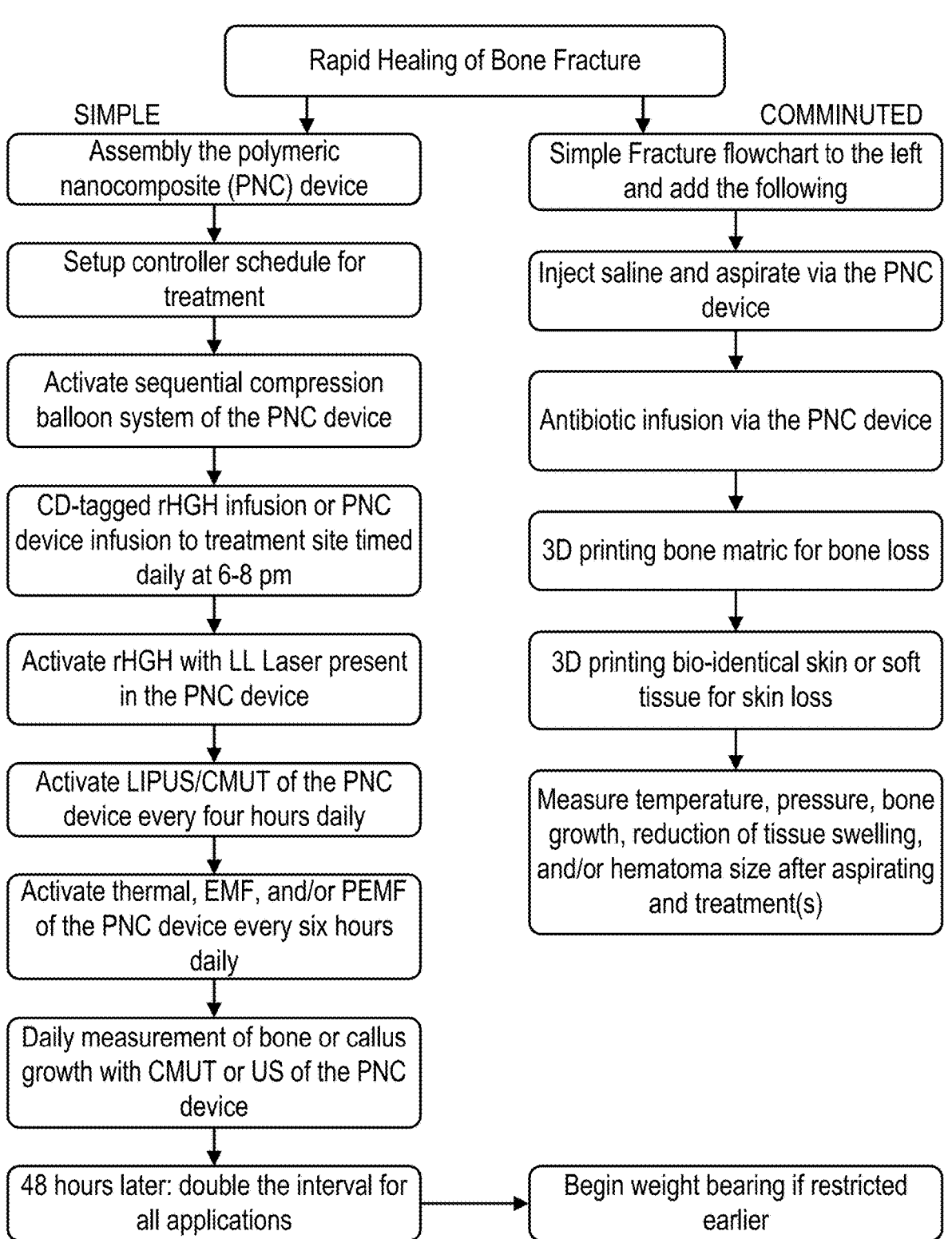
FIG. 11 is a flow chart of steps for rapid healing of simple bone fractures and comminuted bone fractures.

With reference to the flowchart of FIG. 10, methods of treating a treatment site using the medical devices 200 are included herein. In one embodiment, the polymeric nanocomposite device 250 includes layer 114 with a CMUT sensor. The treatment can include application of non-invasive low intensity ultrasound through an array of CMUT sensors. Simultaneous or independent application of CMUT using 1D, 2D or 3D can stimulate multidirectional bone and soft tissue growth. The method of treatment can include simultaneous or independent application of EMF/PEMF to stimulate directional or multidirectional bone growth.

The method can include local application of an active agent via the polymeric nanocomposite device 250. The active agent can include growth hormone for promoting bone and soft tissue growth. Example actives include recombinant human growth hormone (rhGH) and human insulin like growth factor I. These can be administered as a liquid or aerosol, individually or in combination (simultaneous or sequential). In another embodiment, the active agent includes antibiotic. The controller 202 operative controls the administration of any active agent. The administration to the target site can be diffuse, selective, or focal. In one embodiment, the controller is configured to deliver rhGH at onset of sleep.

In some embodiments, the method of treatment can include administration of an oral active agent or one that is absorbed through the lungs. Here, the active agent can include vitamins, antibiotics, anti-inflammatoires, pain killers, NSAIDS. In one embodiment, the vitamin is vitamin D 3.

In one embodiment, the application of EMF or PEMF is combined with ultrasound application (selective or diffuse application thereof), pressure application, and administration of growth hormone, insulin like growth hormone factor and vitamins. The application of the ultrasound can be on a schedule of constant or differential doses over a prescribed period of time, especially for areas of a treatment site that require more growth than other areas. The controller's microprocessors can include software configured to calculate the amount, intensity and duration of the ultrasound application to the treatment site, in particular based on parameters sensed at the treatment site by the any one or more of the various sensors included in the polymeric nanocomposite device 250. In one embodiment, the controller 202 is configures to implement PEMF treatments before implementing pulsed CMUT and pulsed pressure therapy.

In some embodiments, the method includes delivery of a one or more medicaments that is synergistic with the ailment of the treatment site. The controller of the medical device can dispense the one or more medicaments at predetermined times based on circadian rhythm manifestations of medical problems, or in a manner that minimizes the dose and duration of treatment needed to achieve therapeutic goals.

In one embodiment, the CMUT is used to assess size of a hematoma, callus formation, or differential bone density etc. As such, the CMUT is being used as a receiver for the transfer of signals/data back to the controller, thereby providing a feedback loop. The controller can be configured to determine fracture alignment from the CMUT signal/data, which can then be used by the controller to adjust or implement preferential pressure application to the treatment site. The preferential pulse-carrying insulated CDT's/CNT's will transfer continuous or pulsed ultrasound depending on application. The intensity of ultrasound and wavelength will be determined by need such as strength and penetrating distance. Other technology to transfer ultrasound energy such as polymer coated metal or non-metal, fiberoptic or light transmitting material (LED's) or sound transmitting channels (US transmission) will be installed in the controller and/or at least layer 114 of the polymeric nanocomposite device 250.

With reference to the flow chart of FIG. 10, the controller can be configured, via software stored in its memory or via instructions communicated from an external device to the controller, to provide selective local, focal, or generalized interventions based on changing growth measured for the treatment site, including growth of bone and/or tissue. The controller is configured to execute a treatment schedule, which can include any one or more of the treatments discussed above. For example, the treatment schedule can include one or more of activation of a compression balloon system, infusion of active agents, activation of the activation agent if required, a first periodic application of LIPUS/CMUT, a second periodic application of thermal of EMF (regular or pulsed), injection of saline, aspiration of the treatment site, infusion of an antibiotic, 3-D printing of bone matrix, 3-D printing of bio-identical skin or soft tissue. This sequence of events and information related to such events are all stored using blockchain technology and NFTs. This data utilizes Web3 and Decentralized Finance (DeFi) or conventional methods to log each process and its associated billing in the hospital system or healthcare facility so as to provide error-free charging of financial aspect of the technology and its use to third party insurers and payors.

Figure 12:
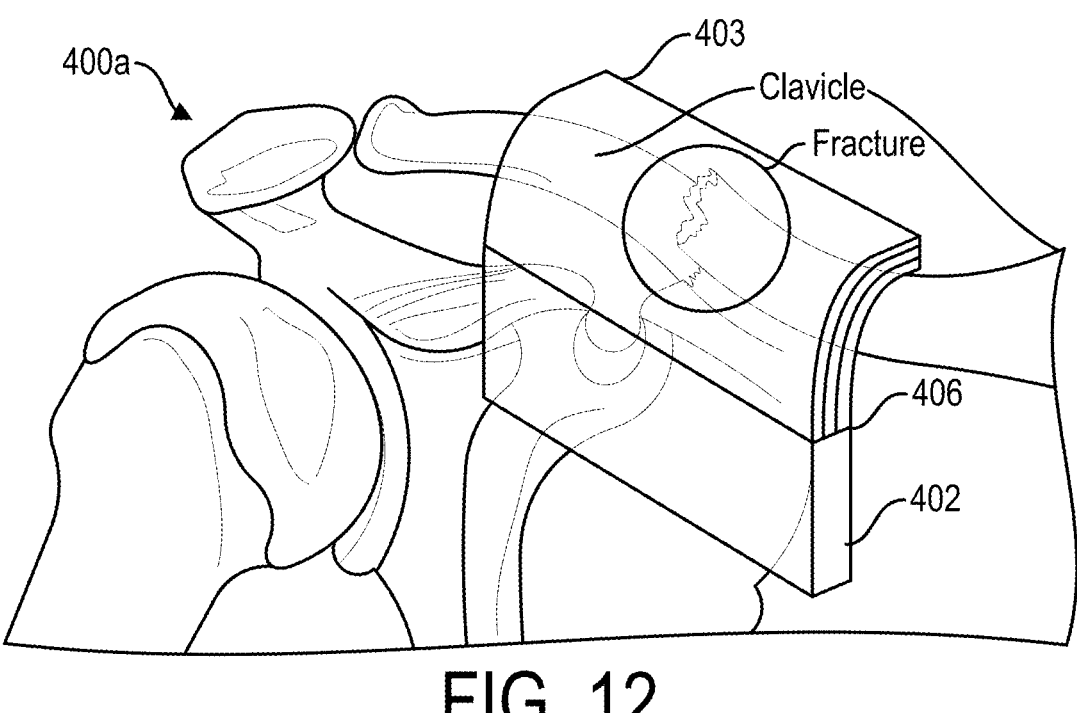
FIG. 12 is a perspective view of an embodiment of a medical device that includes the polymeric nanocomposite device configured to cover a clavicle fracture.
Figure 13:
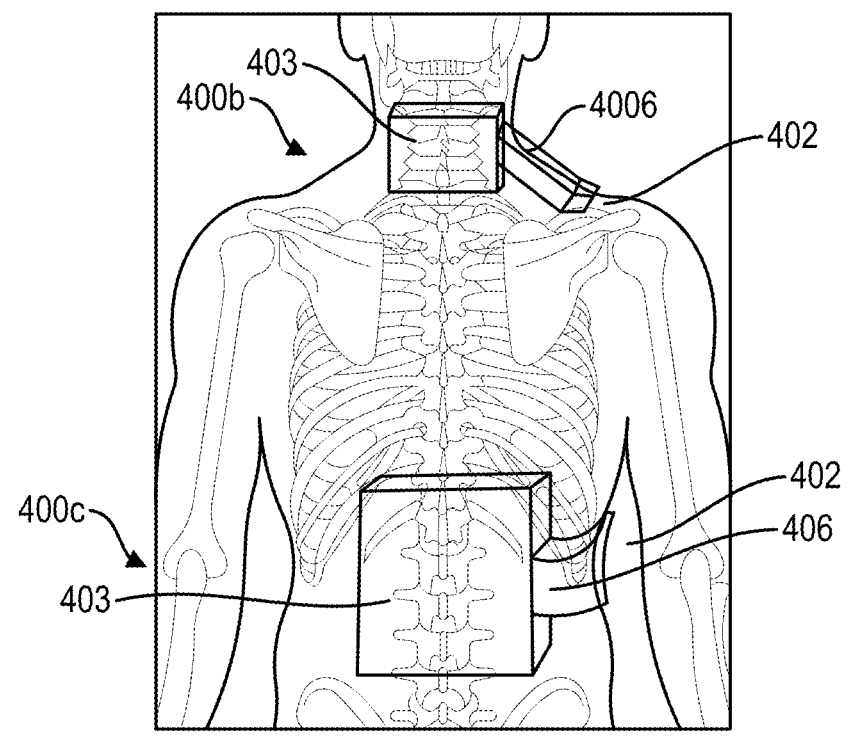
FIG. 13 is a perspective view of two separate embodiments of medical devices for spine fractures that each include a polymeric nanocomposite device.
Figure 14:
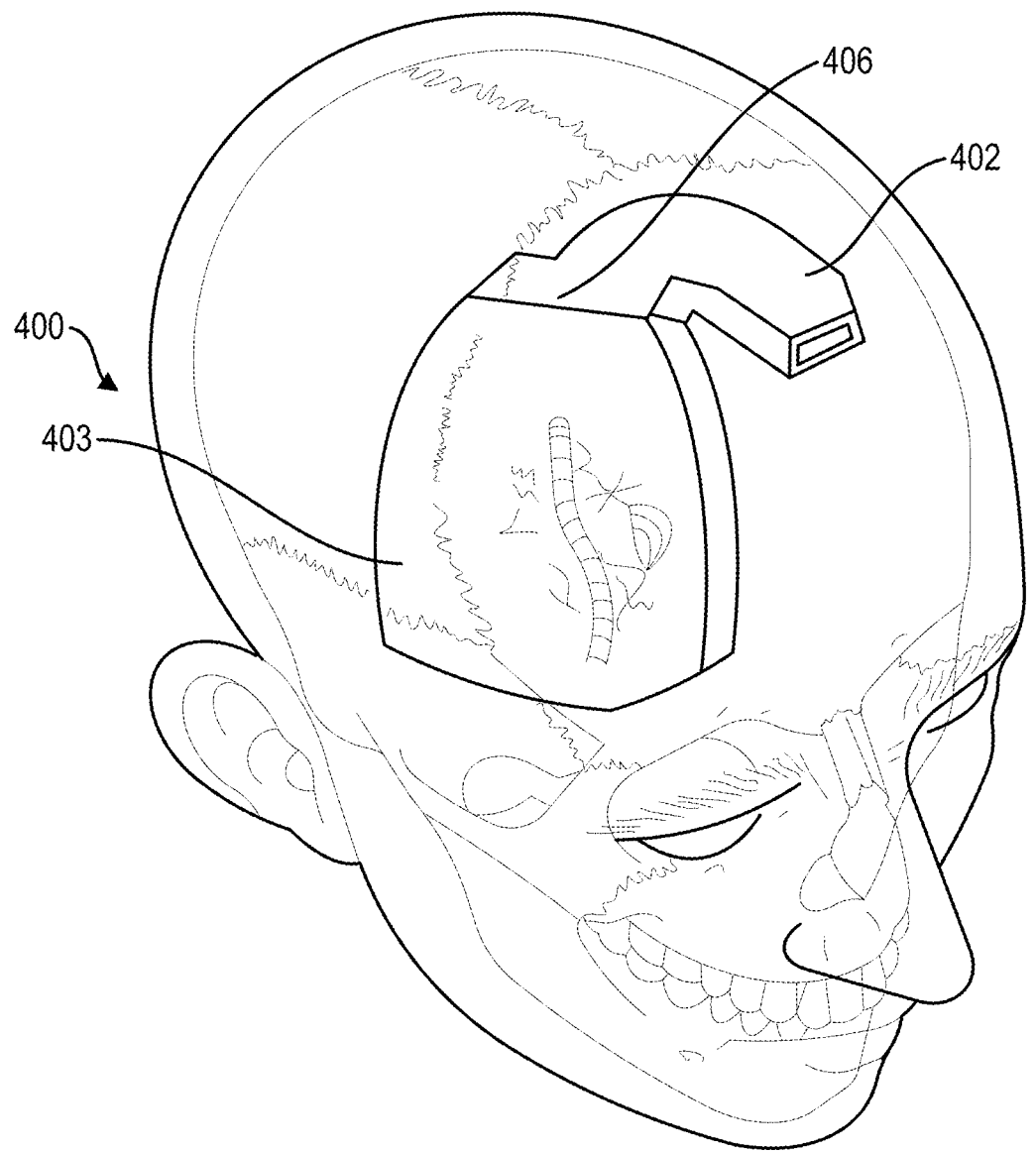
FIG. 14 is a perspective view of an embodiment of a medical device that includes the polymeric nanocomposite device configured to cover a skull fracture.

Turning now to FIG. 12-14, various medical devices, generally referred to by reference number 400, are shown that are configured with treatment site coverings 403 shaped to conform to various bone fractures, such as a clavicle fracture in FIG. 12, spinal fractures in FIG. 13 and a skull fracture in FIG. 14. Each medical device 400a-d has a controller 402 in operative communication via a tether 406 which forms an operative junction to the treatment site covering 403. Each treatment site covering comprises a polymeric nanocomposite device according to any of the embodiments disclosed herein. The treatment site coverings 403 instead of being a wrap or band are configured more as a patch shaped to cover the fracture. As discussed above, the treatment site covering 403 can have a cast 204 as an exterior surface thereof. The controller 402 is operatively coupled to the polymeric nanocomposite device 203 and can be removably attached thereto. The controller can be removably attached to the user or the cast by any fastening means known or herein after developed while the fracture is healing. A few example fastening means include a strap with hook-and-loop material, hook-and-loop material, brackets with bolts or screws, wherein the cast has the brackets, and the like. The controller 402 houses all the electronics discussed above for any of the embodiments thereof.

Octagonal quantum micro-chiplets (OMCs) are made as follows: artificially birthed atomic scale defect carbon (AB-ASDC) is harvested from carbon rich sources like diamond, graphene, and graphite (artificial atoms) and then suspended in octagonal cubicles as plasma. We create the ABASDC plasma to build octagonal quantum bits (OCUBITS). OCU-BITS become the heart of quantum processing that is even greater than quantum CUBITS (cubes) built into QMCs. Multiple octagons are put together in a beehive cluster to create a sheet, which we call the octagonal quantum micro-chiplets. The OMC is integrated with a photon integrated circuit, which we refer to as an OMC/PIC (PIC). More specifically, Neodymium (YAG) Laser treatment of a carbon substrate (Diamond dust, Graphene) is conducted to release hot carbon plasma rich in ABASDC. ABASDC lacking an electron are separated from stable carbon atoms. They form ABASDC plasma. The mass of artificially birthed atomic scale defect carbon (ABASDC) is 12 Daltons. Next, the plasma is cooled. For example, by rapid cooling of the plasma at −20° C. to −40° C. to reduce the internal temperature of the carbon plasma to thermally acceptable value in medical applications. Next, we build SLNT or DLNT or CD octagonal cubicles. This is done using multiple CD/CT with internal dimensions that can accommodate 1-1000 ABADC. Octagonal shape is ideal but other shapes like cube, tube or globe may yield better results in specific applications. Then, we inject cold carbon plasma into SLNT or DLNT Octagon, and we seal Octagon with SLNT, DLNT or CD. In another embodiment, long run of SLNT/DLNT tube may be used to create a tubular structure to inject Cold Carbon Plasma and then seal the tubular structure with end plates of CD or NT. In another embodiment, cold carbon plasma (ABASDC) is injected into multiple octagons or multiple tubes that are already built into a sheet or patch for specific applications and then are sealed simultaneously as well. Thereafter, Amalgamation of multiple octagons placed side by side into multi-layered sheets of octagons to create an OMC. Amalgamation of multiple tubes into a flat sheet, round globe or any other shape configuration based on specifics of application. Amalgamation may be performed prior to injection as described above. The thickness of the sheet or patch is 10 μm to 1000 μm and radius of the globe may be similar. It could be larger in another embodiment and varied shapes.

A graphene sheet or an aluminum nitride sheet can be used as a structural matrix (SM) for an OMC/PIC layer. Other materials may also be used depending on application. The structural matrix, in whatever shape is desired, is stamped with the OMC or has the OMC glued thereto. Then, another structural matrix is stamped to the other surface of the OMC or is glued to the OMC to create a sandwich (SM-OMC-SM). This can then be placed as the core 167 in FIG. 5.

The OMC/PIC is then placed or stamped or glued to MVD-PTFE (Matrix Variable Density Polytetrafluoroethylene) sheet or globe or shape that mimics the OMC/PIC shape. Another layer or multiple other layers of similar MVD-PTFE are placed on all other sides of the OMC/PIC; thus, creating a Hybrid Multifunctional Polymer Matrix (HMFPM). In another embodiment they are enclosed into PI-POSS hybrid SMP (thermoset). HMFPM or OMC/PIC shape can be rectangular, cube, globe or have a structure of any other shape or size that is appropriate for application. Any other material source may be used to cover the OMC/PIC such as aluminum nitride (prior art) or graphene layers or cellulose or a 3D printed bio-degradable resin. MVD-PTFE can be painted to desired thickness over OMC/PIC in another embodiment.

The controller is configured to use blockchain technology. For example, the blockchain can be used to record data, provide continuous tracking of the data (provides an immutable ledger of the data collected in real time. Some of the data collected includes images, tissue temperatures, tissue pressure, arterial doppler ultrasound blood flow characteristics, venous blood flow and clot formation, bone callus formation, bone strength, bone alignment imaging.

All the data that is available to every sensor will be stored in the system memory or in the blockchain technology, as discussed above. The system memory is non-transitory and may be present in the polymeric nanocomposite device 250, the controller 202, or sent to an external memory device (not shown) for storage. If the external memory device is used, the data will be wirelessly transferred thereto and can be transferred or directly stored in a Cloud based database. The stored data can be accessible by or transferred to a medical processional. In one embodiment, the data is accessed through a smart app downloadable to an electronic device, such as a cell phone, tablet, computer, etc. The medical professional can assess satisfactory growth and alignment of bones. This is critical as the healing process is going to be accelerated and a 6-10-week timeline will very likely be reduced to 2-3 weeks. Decision to change any component of the method of treatment can be followed by remote, algorithmic, or manual transmission to the external controller station and from there or directly to the controller 202 of the medical device 200. This data will be used to adjust the method of treatment, such as synchronization of EMF/PEMF and pressure pulse or continuous pressure applications or both thereof synchronized with CMUT or dispensing of an active agent.

The devices and methods of treatment disclosed herein accelerate healing such that a typical 6 to 10 week healing period under standard treatment methods is shortened to 1 to 3 weeks.

The pressure sensors and doppler ultrasound from the CMUT are used to detect arterial blood flow and tissue perfusion, which can enable intervention to prevent amputation of limbs. Also, it enables the detection of early deep vein thrombosis for intervention to pulmonary thromboembolism. Signals from a graphene CMOS sensor doped with lead sulfide (PbS) can be received by the controller and the controller is configured to use this information to detect tissue oxygen levels, for early detection of tissue necrosis and hypoxemia and time for intervention.

It should be noted that the embodiments are not limited in their application or use to the details of construction and arrangement of parts and steps illustrated in the drawings and description. Features of the illustrative embodiments, constructions, and variants may be implemented or incorporated in other embodiments, constructions, variants, and modifications, and may be practiced or carried out in various ways. Furthermore, unless otherwise indicated, the terms and expressions employed herein have been chosen for the purpose of describing the illustrative embodiments of the present invention for the convenience of the reader and are not for the purpose of limiting the invention. Having described the invention in detail and by reference to preferred embodiments thereof, it will be apparent that modifications and variations are possible without departing from the scope of the invention which is defined in the appended claims.

What is claimed is:

1. A medical device comprising:
a controller in operative communication with a polymeric nanocomposite treatment device, the polymeric nano-composite treatment device comprising:
  a layered construction having a top layer and a bottom layer both comprising a matrix variable density polytetrafluoroethylene, a layer of carbon nanostructures juxtaposed to one each of the top layer and the bottom layer, and an electronic network layer between the top layer and the bottom layer,
wherein the electronic network layer comprises a quantum micro-chiplet QMC or an octagonal quantum micro-chiplet integrated with a photonic integrated circuit.

2. The medical device of claim 1, further comprising a tether operatively connecting the controller to the polymeric nanocomposite treatment site device.

3. The medical device of claim 2 wherein the controller is mateable to a first end of the tether and is lockable thereto by a primary lock comprising an expandable male member of either the controller or the tether and a secondary lock configured to opened before the primary lock can be opened.

4. The medical device of claim 3, wherein the expandable male member comprises a compression spring in compression between radially opposing drivers, and the radially opposing drivers are in operative mechanical communication with a security nut, wherein rotation of the security nut activates opposing rods to push the radially opposing drivers toward one another, thereby compressing the compression spring and reducing the size of the expandable male member to render it removable from either the controller or the tether.

5. The medical device of claim 2, wherein the tether comprises carbon nanostructures configured for electrical and/or thermal communication between the controller and the polymeric nanocomposite treatment device.

6. The medical device of claim 2, wherein the tether comprises electrical connections and conduits configured for operative communication between the controller and the polymeric nanocomposite treatment device.

7. The medical device of claim 1, wherein the electronic network layer further comprises a power source in electrical communication with the quantum micro-chiplet and the photonic integrated circuit.

8. The medical device of claim 7, wherein the electronic network layer comprises one or more of a sensor module, an electromagnetic field module, robotics module, an intravascular ultrasound module, and a vacuum module.

9. The medical device of claim 8, wherein the sensor modules comprise one or more of a capacitive micromachined ultrasonic transducer (CMUT), a complementary metal-oxide-semiconductor (CMOS) based sensor, an infrared sensor, a fiberoptic sensor, a radioisotope sensor, a temperature sensor, and a pressure sensor.

10. The medical device of claim 1, wherein the layered construction of the polymeric nanocomposite treatment device further comprises one or more of a sensor module, an electromagnetic field module, robotics module, an intravascular ultrasound module, and a vacuum module as a discrete layer interleaved by juxtaposed layers of carbon nanostructures positioned above or below the electronic network layer.

11. The medical device of claim 10, wherein each discrete layer is in operative communication with the electronic network layer.

12. The medical device of claim 1, further comprising a treatment site covering configured to hold the polymeric nanocomposite treatment device against a treatment site of a user.

13. The medical device of claim 12, wherein the treatment site covering is selected from the group consisting of a wrap, a band, a brace, a cast, and a bandage.

* * * * *